United States Patent
Toniolo et al.

(10) Patent No.: US 9,675,312 B2
(45) Date of Patent: Jun. 13, 2017

(54) APPARATUS FOR CARRYING OUT AN EXAMINATION AND BIOPSY ON THE BREAST OF A PATIENT

(71) Applicant: I.M.S. Internazionale Medico Scientifica S.r.l., Sasso Marconi (IT)

(72) Inventors: Bruno Toniolo, Sasso Marconi (IT); Achille Albanese, Marzabotto (IT); Paolo Vignoli, San Giovanni in Persiceto (IT)

(73) Assignee: I.M.S. Internazionale Medico Scientifica S.r.l., Sasso Marconi (IT)

( * ) Notice: Subject to any disclaimer, the term of this patent is extended or adjusted under 35 U.S.C. 154(b) by 0 days.

(21) Appl. No.: 13/866,814

(22) Filed: Apr. 19, 2013

(65) Prior Publication Data
US 2013/0281843 A1     Oct. 24, 2013

(30) Foreign Application Priority Data

Apr. 24, 2012    (IT) .............................. BO2012A0227

(51) Int. Cl.
*A61B 6/00*     (2006.01)
*A61B 6/02*     (2006.01)
*A61B 6/04*     (2006.01)

(52) U.S. Cl.
CPC .............. *A61B 6/502* (2013.01); *A61B 6/025* (2013.01); *A61B 6/0435* (2013.01); *A61B 6/4452* (2013.01); *A61B 6/4258* (2013.01)

(58) Field of Classification Search
None
See application file for complete search history.

(56) References Cited

U.S. PATENT DOCUMENTS

| 4,905,266 A | * | 2/1990 | Kuck et al. .................... 378/177 |
| 5,305,365 A | | 4/1994 | Coe |
| 5,872,828 A | * | 2/1999 | Niklason ................ A61B 6/025 378/23 |

(Continued)

FOREIGN PATENT DOCUMENTS

| EP | 387475 | 9/1990 |
| EP | 1428473 | 6/2004 |
| WO | WO 2011153555 A2 * | 12/2011 |

OTHER PUBLICATIONS

Webster's Dictionary Entry for "Reciprocating Motion" (http://www.webster-dictionary.org/definition/Reciprocating%20motion).
*

(Continued)

*Primary Examiner* — Christopher Cook
*Assistant Examiner* — Carolyn Pehlke
(74) *Attorney, Agent, or Firm* — Shuttleworth & Ingersoll, PLC; Timothy J. Klima

(57) ABSTRACT

An apparatus for carrying out an examination on the breast of a patient, includes an analysis head including at least one radiation detection device, configured to receive and detect radiation on a detection plane and at least one X-ray source to emit a corresponding beam of X-rays towards the detection plane. A first frame is provided with a floor support; a second frame supports the analysis head; and a third frame is connected to the first frame so that it can be moved from a horizontal position to a vertical position, and which supports the second frame. A movement mechanism moves the third frame from the horizontal position to the vertical position.

17 Claims, 8 Drawing Sheets

(56) References Cited

U.S. PATENT DOCUMENTS

| | | | |
|---|---|---|---|
| 6,419,390 B1* | 7/2002 | Landis-Lowell | A61B 6/0414 378/208 |
| 7,634,050 B2 | 12/2009 | Muller et al. | |
| 8,842,806 B2* | 9/2014 | Packard et al. | 378/37 |
| 2002/0122533 A1 | 9/2002 | Marie et al. | |
| 2004/0109529 A1* | 6/2004 | Eberhard | A61B 6/025 378/23 |
| 2007/0133738 A1* | 6/2007 | Zimmermann | A61B 6/4429 378/37 |
| 2009/0135996 A1* | 5/2009 | Muller | A61B 6/502 378/37 |
| 2010/0208865 A1* | 8/2010 | Sendai | A61B 6/022 378/28 |
| 2010/0234727 A1* | 9/2010 | Yoshizawa et al. | 600/431 |
| 2012/0106705 A1* | 5/2012 | Mikami et al. | 378/70 |
| 2012/0207282 A1* | 8/2012 | Goto | A61B 6/4233 378/197 |

OTHER PUBLICATIONS

Italian Search Report dated Dec. 11, 2012 from counterpart application.

* cited by examiner

APPARATUS FOR CARRYING OUT AN EXAMINATION AND BIOPSY ON THE BREAST OF A PATIENT

This application claims priority to Italian Patent Application BO2012A000227 filed Apr. 24, 2012, the entirety of which is incorporated by reference herein.

BACKGROUND OF THE INVENTION

This invention relates to an apparatus for carrying out an examination on the breast, in particular for carrying out mammography and/or tomosynthesis ("digital breast tomosynthesis", DBT), and biopsy.

There are known apparatuses for mammography/tomosynthesis that comprise a source configured to emit X-rays and a detector configured to receive the X-rays emitted by the source.

It should be noted that the patient's breast being analyzed is interposed between the X-ray source and the detector in such a way that the X-rays pass through it.

These apparatuses can also be easily equipped with a system for stereotaxic biopsy. This system consists of a method for the computation of the exact position of a region of interest inside the breast, by means of the acquisition of a number of images at predetermined angles with respect to a rotation fulcrum, and of a probe (motor-driven or not) for extraction of tissue by incision.

The two main approaches for stereotaxic biopsy are in the prone position and the vertical position.

An apparatus for mammography and tomosynthesis generally allows a stereotaxic biopsy to be carried out with the patient positioned with the trunk vertical, standing or seated.

A biopsy performed in the vertical position makes it possible to reduce the time of the procedure, and makes the procedure easier if the patient has small breasts.

It is, however, preferable to also have the possibility of performing the biopsy in the prone position (with the patient lying on a dedicated table above the system), since in most cases this method increases patient comfort, reducing the risk of movement and extending accessibility to the breast. The prone table allows two people to work comfortably around the patient, making the procedure more efficient. It has also been demonstrated that vasovagal reactions (fainting) occur less frequently in the prone position.

Prone biopsy systems are generally available on dedicated apparatuses, which therefore require additional space and expense with respect to vertical mammography systems and which thus cannot be accommodated in all health settings.

The patent document EP0387475 describes an apparatus able to perform mammography and stereotaxic biopsy both in vertical position and in prone position, but this apparatus is not able to perform tomosynthesis or other types of breast examination. Moreover, in the above apparatus the movement from the vertical position to the prone position is achieved in such a way that the dimensions of the machine sometimes hinder the performance of the prone biopsy.

A further requirement is thus the availability of an apparatus with a structure that is not too bulky for it to be used in not particularly spacious settings.

The patent document U.S. Pat. No. 5,305,365 describes an example of a machine for mammography that can perform a partial rotation of the analysis head, for a very limited angle, to favor the performance of the mammography on the patient.

This machine comprises a load-bearing frame that supports a mobile analysis head between a vertical position, in which the patient undergoes analyses while standing, and an inclined position, in which the patient undergoes analyses with the chest in a vertical position. Although this system has limited dimensions, its purpose does not correspond to the requirement expressed above that is to say of providing an apparatus of simple design which allows the medical staff to perform examinations on the patients breast in the erect and prone positions.

Nuclear medicine is distinguished from radiology by the fact that it does not have a radioactive source outside the patient (transmission imaging), but the patient him/herself becomes the source of radiation (emission imaging) by administration of a radioactive drug, and it is not therefore a measure of radiation attenuation that passes through the body, but a measure of distribution and intensity of the radiation emitted by the body. The analysis head for a nuclear medicine application requires one or more gamma ray detectors, coupled to a collimation system (physical or electronic by means of coincidence detection) which makes it possible to select and identify the source direction of the photon.

As already indicated for biopsy examinations, nuclear medicine tests can also favor the prone or erect position depending on the duration of the test and the specific application. The possibility of using an apparatus in both positions, not limited to radiological applications, thus makes the invention even more useful.

An additional advantage is that tomosynthesis can be performed in the prone position, so that the image obtained can be used as a guide for the subsequent biopsy sample.

This invention also intends to provide a particularly versatile apparatus that can be used to perform a plurality of examinations on the breast.

With a different analysis head in addition to or replacing the combination between X-ray source and X-ray detector, the same mechanical structure can be used for other types of breast examinations, such as for example (but not only) nuclear medicine examinations.

SUMMARY OF THE INVENTION

Accordingly, this invention achieves the aims indicated above with an apparatus for breast examinations comprising the technical features described in one or more of the appended claims.

BRIEF DESCRIPTION OF THE DRAWINGS

The technical characteristics of the invention, with reference to the above aims, are clearly described in the claims below and its advantages are apparent from the detailed description which follows, with reference to the accompanying drawings which illustrate a preferred embodiment of the invention provided merely by way of example without restricting the scope of the inventive concept, and in which:

DESCRIPTION OF THE PREFERRED EMBODIMENTS

Figure 1:
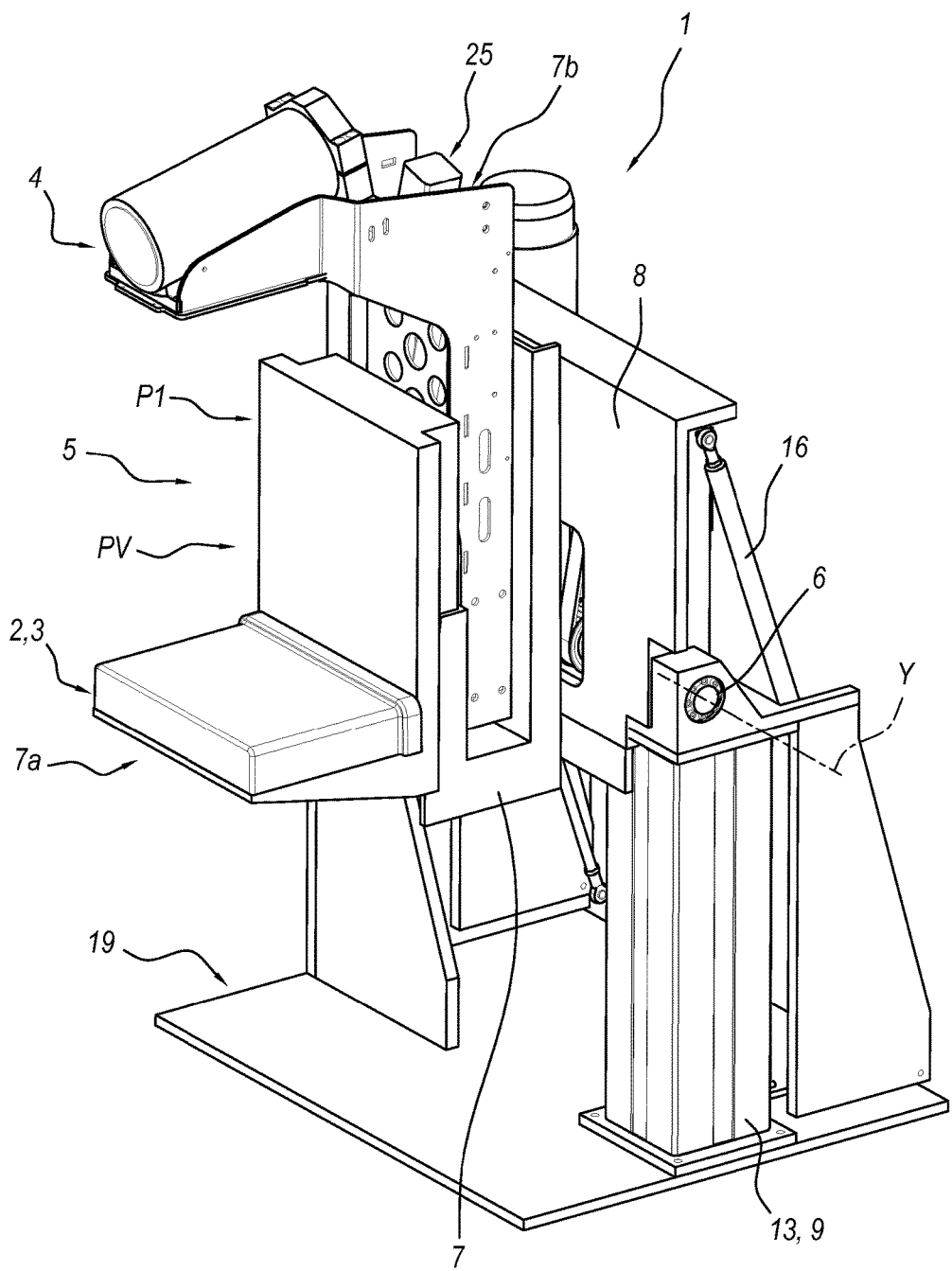
FIGS. 1 and 2 are perspective views of a the apparatus acct according to this invention in a first configuration.

With reference to the accompanying drawings, the numeral 1 denotes an apparatus for mammography according to this invention. According to the invention, the apparatus 1 (hereinafter indicated as the machine 1) makes it possible to perform an examination on the breast of a patient (preferably but not exclusively it makes it possible to perform mammography and/or tomosynthesis of a patient's breast and biopsy).

Below is a description of a preferred, non-limiting embodiment of the apparatus shown in FIGS. 1-6.

This apparatus comprises an analysis head 5 equipped with an X-ray detector device 2, designed to receive and detect X-rays on a detection plane 3.

The analysis head 5 preferably comprises one (or a plurality of) X-ray source (sources) 4 to emit a corresponding X-ray beam towards the said detection plane 3.

This apparatus comprises a first frame 6 provided with floor support means 9.

In the embodiment shown, the first frame 6 preferably comprises a horizontal crosspiece 23.

The horizontal crosspiece 23 defines the upper crosspiece of a portal structure.

The horizontal crosspiece 23 also comprises housings for a shaft 21 which will be better described below.

These floor support means 9 comprise a telescopic column 13, as shown in FIG. 1.

The floor support means 9 more preferably comprise a pair of telescopic columns 13 which support the first frame 6.

Preferably but not exclusively, these telescopic columns 13 bilaterally support the first frame 6, in particular they support the horizontal crosspiece 23.

These columns 13 are connected at a first (lower) end to a floor support plate 19 and at a second end to the first frame 6.

According to another aspect, the apparatus 1 comprises means for the vertical movement 12 of the first frame 6, configured to move the first frame 6 vertically with respect to the ground.

In the embodiment shown in the accompanying figures, the means for vertical movement 12 comprise an actuator, not visible as it is hidden inside the telescopic column 13, configured and activatable to allow raising of the first frame 6 with respect to the ground.

It can in fact be observed that the detection plane 3 can be positioned at the correct height for the patient on whom the examination is to be performed.

The apparatus 1, provided with mean of vertical movement 12, allows the medical staff to adjust the height of the detection plane 3 to accommodate patients of any height, as well as patients with limited walking ability (wheelchair users).

It can be seen in FIG. 1 that only one column 13 is present; on the opposite side to the first frame 6 it is connected to the plate 19 by means of a gas spring 20.

The column 13, the gas spring 20 and the plate 19 together define the floor support means 9.

According to another embodiment, not shown, the floor support means 9 can consist of a pair of columns 13.

The apparatus 1 also comprises a second frame 7 supporting the analysis head 5.

In this invention, the expression frame is intended as one or more elements acting as structural supports.

The apparatus 1 also comprises a third frame 8 connected (in the preferred embodiment, hinged) to the first frame 6 in such a way that it is mobile between a substantially horizontal position PO and a substantially vertical position PV.

The fact that the third frame 8 is mobile between these positions allows the apparatus to be set up in two configurations, so as to perform examinations of the breast with the patient in a prone position (when the third frame 8 is in the substantially horizontal position) and erect/seated (when the third frame 8 is in a substantially vertical position).

Preferably, as shown in the accompanying figures, the third frame 8 rotatably supports the second frame 7.

In variants of the apparatus 1 not shown, the second frame 7, which supports the analysis head, is fixed rigidly to the third frame 8.

The second frame 7 is defined by the group of elements that support the analysis head 5.

In the preferred embodiment, the third frame 8 rotates around a horizontal axis Y (clearly visible in the accompanying figures).

In other words, the third frame 8 rotates by 90°.

The horizontal rotation axis Y is positioned below the third frame 8.

When the third frame 8 is in the vertical position PV, the plan dimensions of the apparatus are extremely limited and develop in a substantially vertical direction; this advantageously reduces the overall plan dimensions and increases the working space available to the medical staff.

The apparatus according to claim 1 comprises means of movement 10 of the third frame 8 with respect to the first frame 6, configured to allow rotation of the third frame 8 around the horizontal axis Y.

More in general, these means of movement 10 allow the movement of the third frame 8 between the two positions PO and PV.

Figure 2:
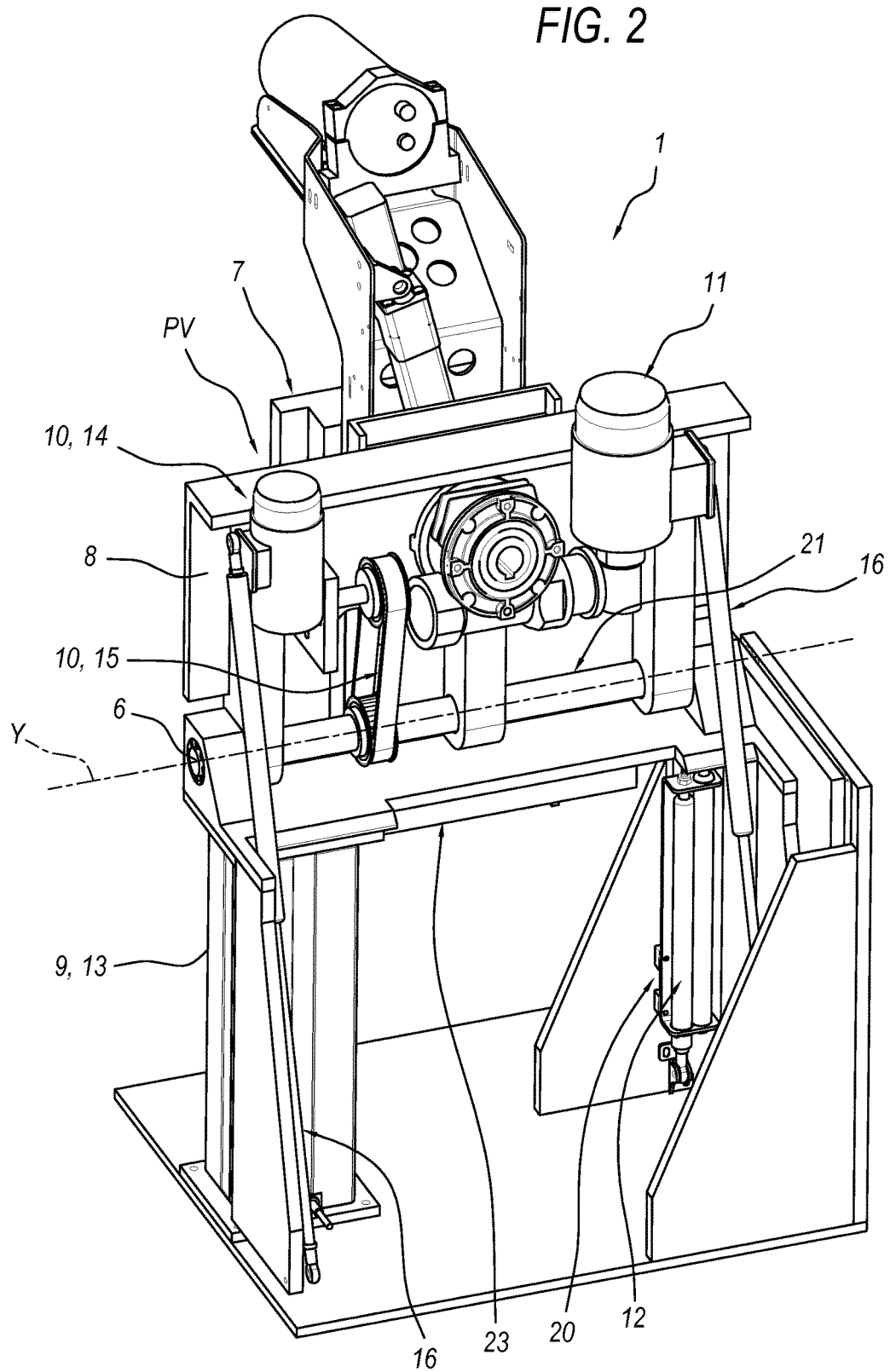

According to the preferred embodiment these means of movement 10, clearly visible in FIG. 2, comprise a motor 14, kinematically coupled to the third frame 8.

In particular, the motor 14 is coupled to the third frame 8 by means of a belt 15.

The belt 15 is kinematically coupled to a shaft 21 (solidly connected to the third frame 8) which develops horizontally.

The axis Y, around which the third frame 8 rotates, is the axis of the shaft 21.

The shaft 21 is rotatably supported by the first frame 6; in particular, the shaft 21 is rotatably supported in the two housings present in the horizontal crosspiece 23.

The shaft 21 is positioned in a lower portion of the third frame 8.

The apparatus 1 preferably comprises at least one pair of spring pistons 16 (or, according to a variant not shown, just one spring piston 16) hinged to the first frame 6 and to the third frame 8 to exert a thrust on the third frame 8 in order to move the third frame 8 to the vertical position PV.

In other words, the spring pistons 16 allow the third frame 8 to be maintained in the vertical position PV: the means of movement 10 must therefore overcome the force exerted by the spring pistons 16 to move the third frame 8 from the vertical position PV to the horizontal position PO.

More in general, the spring pistons act as a pusher device 16, hinged to the first frame 6 and to the third frame 8 to exert a thrust on the third frame 8 in order to move the third frame 8 to the vertical position PV.

The second frame 7 rotates with respect to the third frame 8, in other words it is configured to rotate around an axis K at right angles to the horizontal axis Y.

The axis K preferably has a predetermined distance with respect to the breast support plane 30 (which is positioned above the detection plane 3): this advantageously makes it possible to rotate the breast support plane 30 so that when the detection plane 3 is substantially inclined (rotation of an acute angle with respect to the position in which the plane 30 is horizontal) or vertical (rotation of 90° with respect to the position in which the plane 30 is horizontal), the plane 30 is outside the space occupied by the machine.

One advantage of this aspect is that the operator can more easily perform an examination of the breast with the detection plane 3 in an inclined or vertical position; in particular, the positioning of the breast by the operator is made easier.

Figure 8:
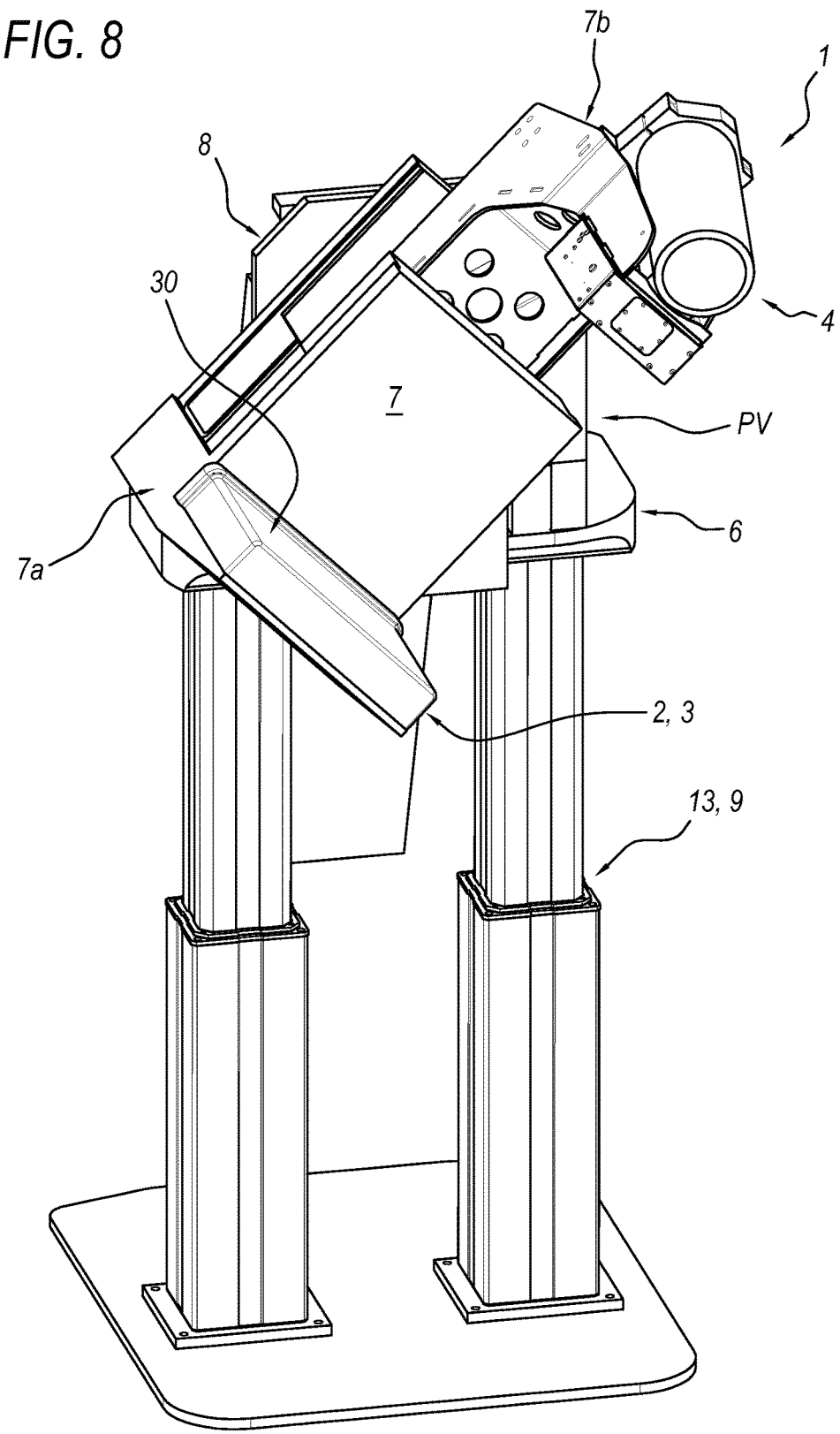
FIG. 8 illustrates the apparatus of FIG. 7 in another configuration.

FIG. 8 clearly shows what is described above, that is to say that the breast support plane 30 can be moved outside the space occupied by the machine.

In particular, FIG. 8 shows the second frame 7 rotated by around 45° around the axis K with respect to the position shown in FIG. 1.

The apparatus 1 comprises means of movement 11 of the second frame 7 with respect to the third frame 8 to allow the rotation of the second frame 7 with respect to the third frame 8 around an axis K at right angles to the horizontal axis Y.

The frame 7 can be positioned at any angle; it can preferably be rotated at least 270°, even more preferably 360°.

Figure 5:
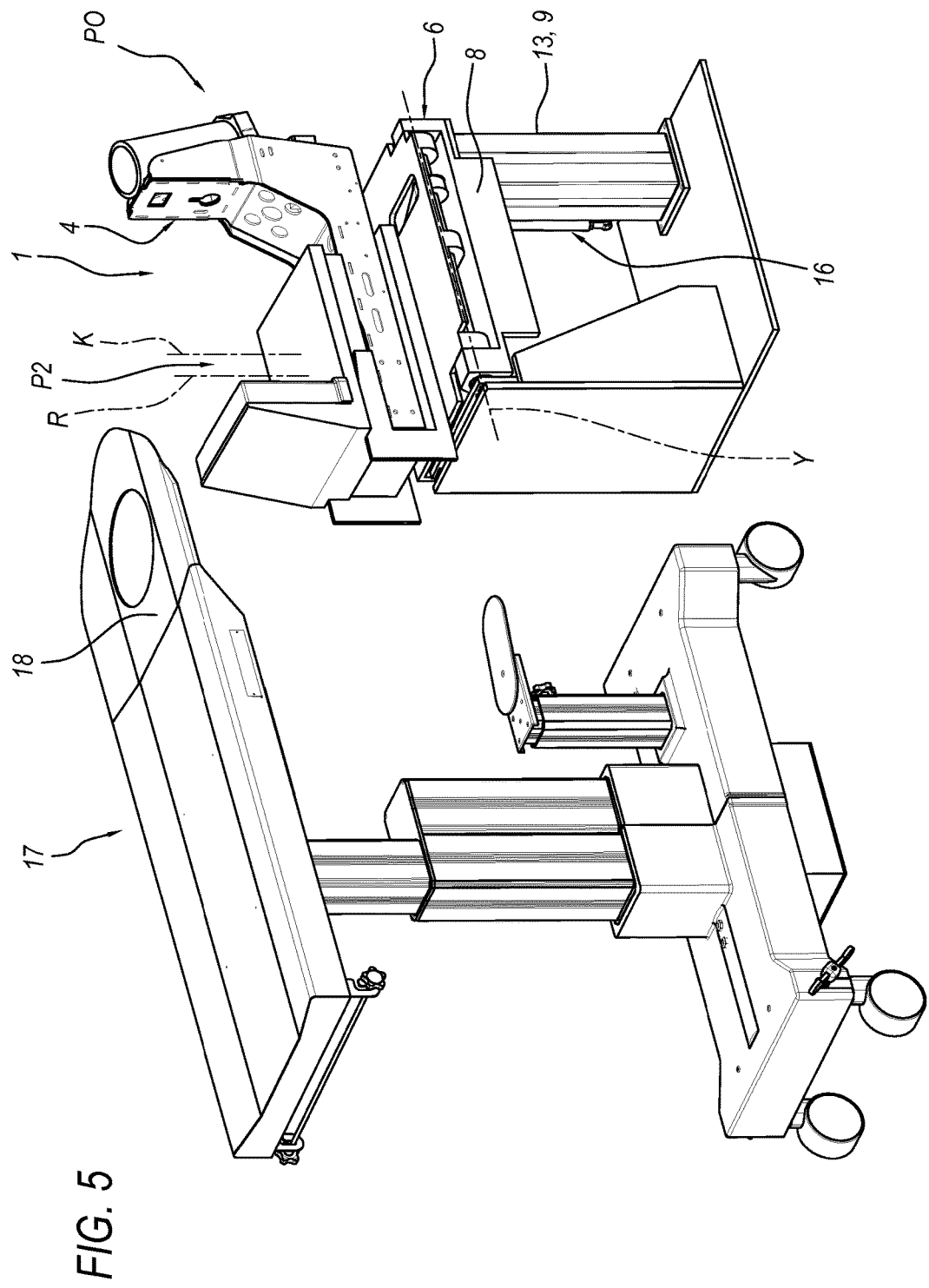
FIG. 5 is a perspective view of a detail of the apparatus from FIG. 1 in a fourth configuration.

These means of movement 11 allow rotation of the second frame 7 in order to position it at any angle desired: by way of examples, FIG. 1 shows a first possible position P1, while FIG. 5 shows a second possible position P2.

According to the embodiment shown, the means of movement 11 comprise a motor and a gear, configured to allow the rotation of the second frame 7 with respect to the third frame 8.

In the example shown, the frame 7 is rotated by 90° between the first position P1 and the second position P2.

The second frame 7 is described below.

It is known that tomosynthesis and stereotaxic biopsy foresee the acquisition of images with the source placed in a plurality of positions with respect to the detection device 2; the apparatus 1 is therefore configured so that the source 4 and the detector 2 are relatively mobile.

In particular, according to this second aspect the second frame 7 comprises a first portion 7a which supports the X-ray detector device 2 and a second portion 7b which supports the X-ray source 4.

This first 7a and second portion 7b are reciprocally mobile to allow movement of the source 4 with respect to the detector device 2.

In particular, the fact that the first 7a and the second portion 7b are reciprocally mobile allows the source 4 to emit a beam of X-rays towards the detection plane 3 in a plurality of positions with respect to the detector device 2.

As regards the second frame 7, the apparatus 1 is configured to allow the rotation (simultaneous and jointly) of the first and second portions 7a and 7b and the relative rotation of the second portion 7b with respect to the first portion 7a.

The rotation of the second portion 7b with respect to the first portion 7a makes it possible to perform tomosynthesis: in fact, by means of this rotation the source 4 can be placed in a plurality of positions with respect to the detector 2 in order to acquire images of the patient's breast in a plurality of positions.

In addition, in the apparatus 1 the axis of rotation R of the second portion 7b with respect to the first, portion 7a is closer to the detector 2 than the axis K of rotation of the second frame 7 with respect to the third frame 8.

The apparatus 1 configured in this way has good balancing of the weights of the analysis head 5, whatever the position of the second frame 7 around the axis K and of the second portion 7b around the axis R.

The apparatus 1 is provided with means of movement 25 of the second portion 7b (which supports the source 4) with respect to the first portion 7a (which supports the detector 2).

In the preferred embodiment, these means of movement 25 comprise an electrical actuator provided with a piston sliding inside a cylinder.

This piston is connected (hinged) to the first portion 7a, while the cylinder is connected (hinged) to the second portion 7b (or vice versa the piston is connected to the portion 7b and the cylinder to the portion 7a).

The longitudinal movement of the piston inside the cylinder causes the rotation of the second portion 7b with respect to the first portion 7a, allowing tomosynthesis to be performed.

FIG. 5 shows a bed 17 used to perform examinations of the breast with the patient in the prone position.

The bed 17 is provided with a patient support surface with an opening 18 to allow the patient to expose her breast downwards, and is provided with a movement system which allows it to be positioned above the apparatus when this is in the PO position, so that the breast can be positioned in correspondence with the analysis head.

It has already been stated, with reference to prior art, that the prone position allows greater patient relaxation with respect to the vertical position. It also prevents the patient from seeing the performance of the examination, and prevents any accidental movements of the patient in the event of lengthy examinations or of fainting.

In addition, performing a biopsy with the patient in the prone position helps the patient to recover after the procedure.

It is possible to arrange the bed 17 in a plurality of positions with respect to the machine, in order to be able to approach the patient's breast from different angles/positions: this allows the biopsy procedure to be performed in the easiest position for the specific case, making it possible to reduce the examination time and to increase the probability of success.

The bed 17 and the apparatus 1 together define a diagnostic system which is also within the scope of the invention.

The apparatus 1 also comprises a control unit (not shown), connected to the detector 2 and to the source 4 to allow image processing.

The apparatus 1 may also comprise a biopsy probe, which can be fixed to the second frame 7 to allow the biopsy procedure to be performed.

This probe comprises a needle which makes it possible to remove organic tissue from the patient's breast.

The probe is connected to the second frame 7 by a movement mechanism 22 with one or more degrees of freedom; the probe is preferably moved by slides (shown in FIG. 6) which allow movement of the needle on three right-angle axes.

Briefly described below is the operation of the apparatus, with reference to a preferred mode of operation, which is not, however, binding.

The advantages of the apparatus 1 can be inferred from this description, the apparatus being able to satisfy the requirements of the medical staff and at the same time to ensure ideal patient relaxation both during the mammography/tomosynthesis procedures and during the biopsy procedure in prone or vertical position.

Figure 3:
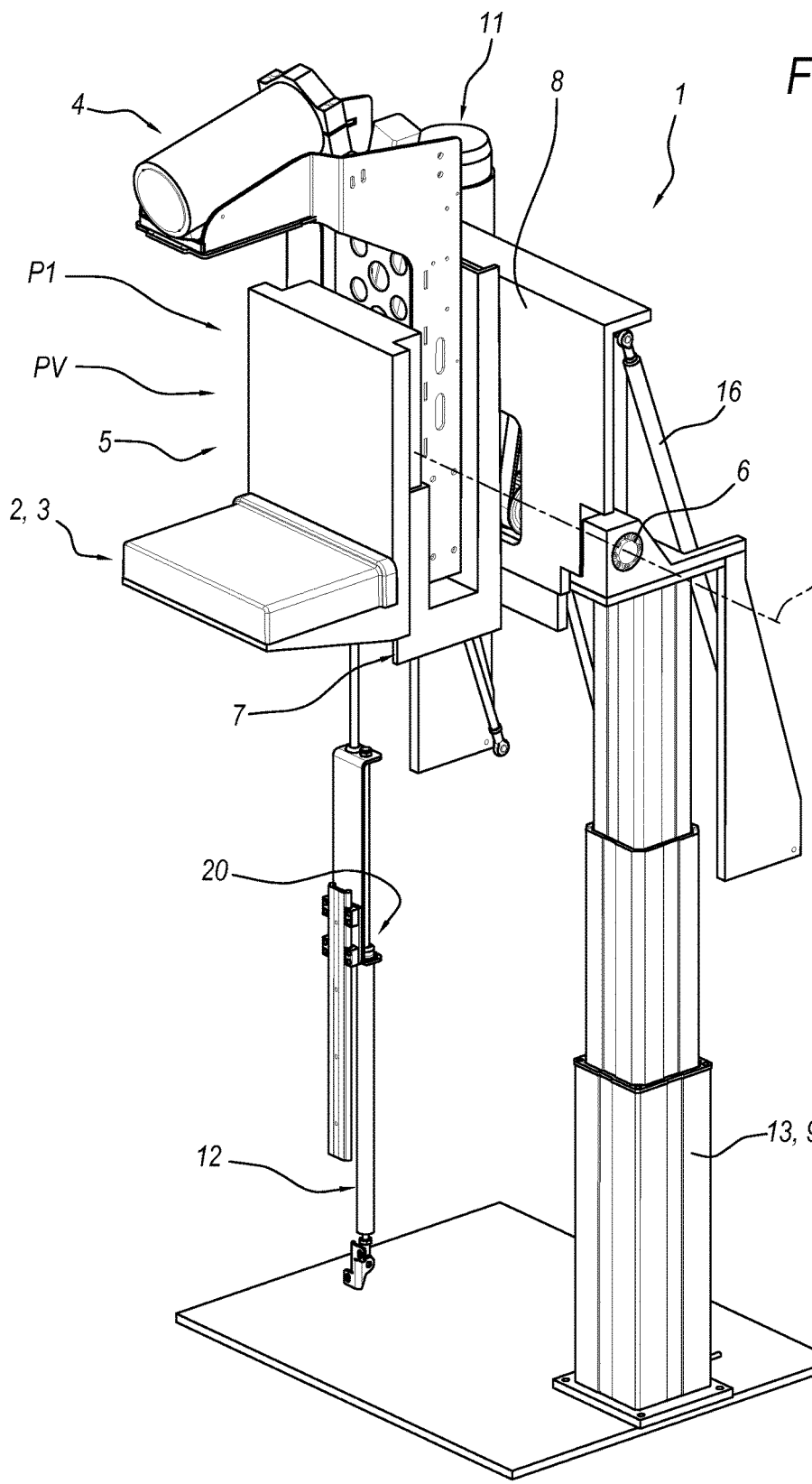
FIG. 3 illustrates a prospective view of the apparatus according to the invention in a second configuration where some parts have been cut away in order to better illustrate others.
Figure 4:
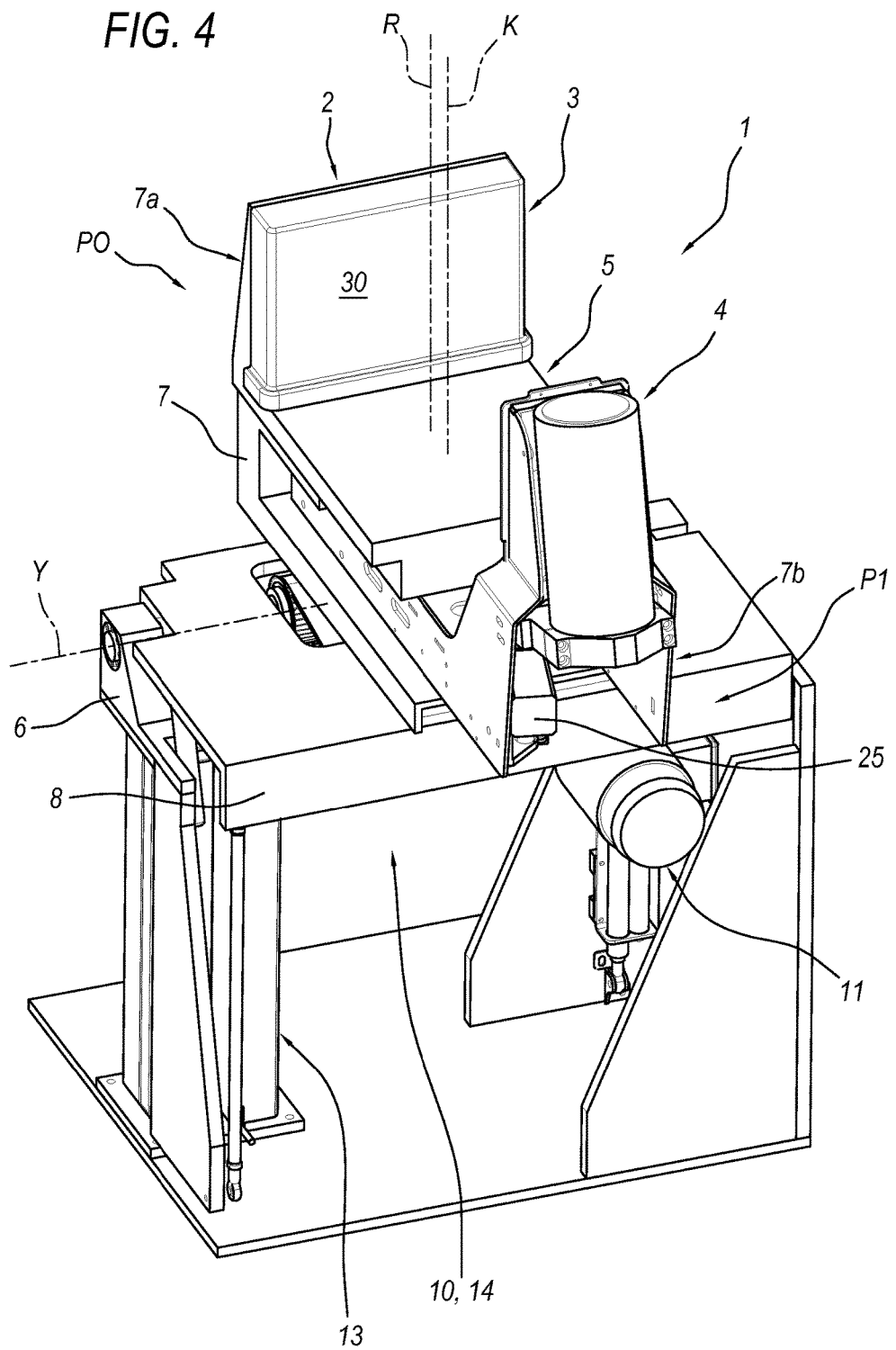
FIG. 4 is a perspective view of a detail of the apparatus from FIG. 1 in a third configuration.

FIGS. 1, 2 and 3 show the apparatus 1 in a configuration designed for mammography or tomosynthesis.

In FIGS. 1 and 2, the apparatus 1 is in a configuration with minimum height of the first frame 6 (in this configuration the first frame 6 is in a proximal position with respect to the ground) while in FIG. 3 the apparatus is in a configuration with maximum height of the first frame 6 (in this configuration the first frame 6 is in a distal position with respect to the ground).

The operator activates the means 12 for vertical movement of the first frame 6 to pass from the minimum height configuration of the first frame 6 to the maximum height configuration of the first frame 6.

These means 12 of vertical movement make it possible to raise/lower the first frame 6, the second frame 7 and the third frame 8 with respect to the ground (in fact, the second frame 7 and the third frame 8 are supported by the first frame 6): this makes it possible to adjust the apparatus 1 according to the height of the patient.

In particular and more specifically, the means 12 of vertical movement act on the first frame 6, which supports both the third frame 8 and the second frame 7.

Activation of the means 12 of vertical movement allows adjustment of the height of the first frame 6 with respect to the ground which is made according to the height of the patient, in order to position the detection plane 3 at the correct height for the patient being examined.

After installing the biopsy probe on the apparatus 1, the medical staff can perform a vertical biopsy on the patient with the machine in the configuration shown in FIGS. 1-3 (third frame 8 in the vertical position, second frame 7 in the position P1).

Figure 6:
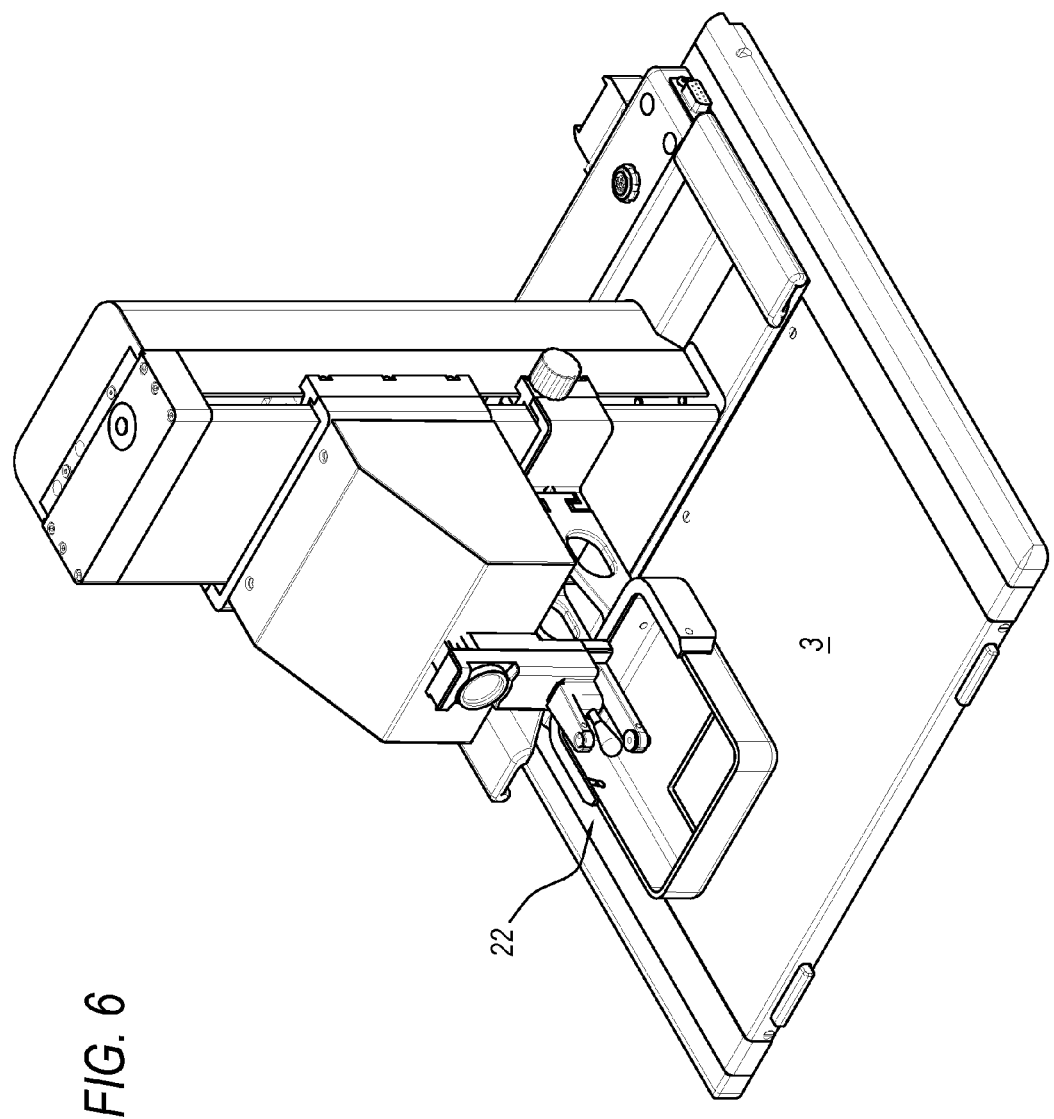
FIG. 6 is a perspective view of an accessory of the machine shown in the preceding figures.

If, on the other hand, it is necessary to perform a prone biopsy, the third frame 8 is rotated 90° with respect to the configuration shown in FIGS. 1, 2 and 3 so that it is in the horizontal position PO (this configuration of the apparatus is shown in FIGS. 5 and 6).

In the horizontal position PO, the second frame 7 can be rotated with respect to the axis K to a desired position (for example, position P1 in FIG. 4 or P2 in FIG. 5) so that the medical staff can position the bed 17, with respect to the machine as required depending on the part of the breast to be biopsied.

In the configuration of the apparatus in which the third frame 8 is in the horizontal position PO, it is possible to carry out a prone biopsy, with the patient lying on the bed 17.

The apparatus 1 according to this invention is advantageously extremely compact.

In particular, the means of movement 10 and 11 are positioned behind the analysis head 5 so that when the third frame 8 is rotated by 90° with respect to the vertical, that is in the position PO, these means 10 and 11 are outside the working area, allowing complete access to the medical staff.

Such a machine is extremely practical and simple and be easily installed even in small examination rooms.

It must in fact be stressed that when the third frame 8 is in the vertical position PV, the plan space is extremely limited and even when the third frame 8 is in the horizontal position PO, to allow a prone biopsy to be performed, the overall space taken up is limited.

This machine is designed with a particularly simple and compact structure: by just rotating the third frame 8 the machine is placed in a configuration that allows a prone biopsy to be performed, maintaining its limited overall dimensions.

The positioning of the means of movement 10 and 11 behind the third frame 8 (and the fact these means 10 and 11 are supported by the this frame 8) means that these means 10 and 11 are located in such a way as not to get in the way of the operator when the third frame 8 is rotated.

Figure 7:
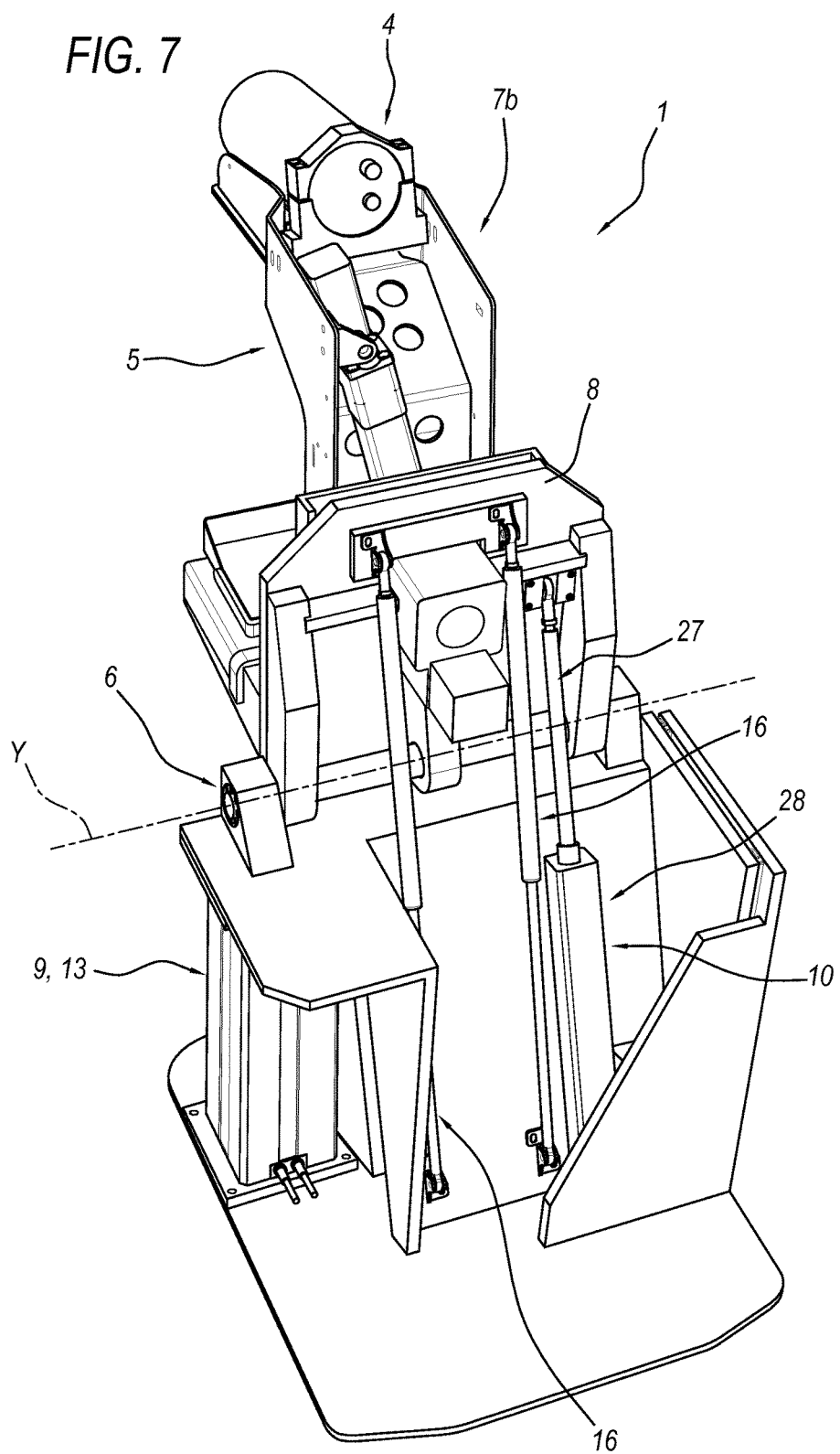
FIG. 7 shows a variant of the apparatus shown in the preceding FIGS. 1-5.

According to another embodiment, shown in FIG. 7, the means for movement 10 of the third frame 8 with respect to the first frame 6 from the horizontal position PO to the vertical position PV comprise a piston 27-cylinder 28 unit.

The piston 27 slides with respect to the cylinder 28.

In the embodiment shown in FIG. 7, the piston 27 is connected (hinged) to the third frame 8, while the cylinder 28 is connected (hinged) to the first frame 6.

According to a variant not shown, the piston 27 is connected (hinged) to the first frame 6, while the cylinder 28 is connected (hinged) to the third frame 8.

The piston 27-cylinder 28 unit thus forms an actuator, connected to the third frame 8 and to the first frame 6 to allow the movement of the third frame 8 with respect to the first frame 6.

More in general, the apparatus 1 makes it possible to perform examinations on the breast of a patient.

The apparatus 1 thus more in general comprises an analysis head 5 provided with a radiation detection device 2, configured to receive and detect on a detection plane 3 the radiation passing through the patient's breast (this radiation can be emitted by the breast or by a source forming part of the apparatus 1).

The apparatus 1 can in fact be configured to carry out any type of examination on the breast.

For example, the apparatus 1 can be configured to allow nuclear medicine examinations to be performed.

For this type of examination, the patient must take a so-called radioactive drug so that some of the patient's organs emit radiation outwards.

The apparatus does not, therefore, have to be provided with an X-ray source since in this type of examination, in which the patient has to take a radioactive drug, it is the patient's body that emits the radiation.

According to a variant not shown in the figures, the apparatus 1 is not provided with an X-ray source.

The radiation emitted by the patient's body is detected by the detection device.

As regards biopsy, the following should be pointed out.

The apparatus preferably allows biopsy to be performed by means of the stereotaxic method.

This method foresees that the exact location of the tissue abnormality must be identified through images of the breast acquired at predetermined angles with respect to a rotation fulcrum.

The apparatus 1 according to the invention, as described above, allows biopsy to be performed by means of the stereotaxic method: in fact, the radiation source is rotated with respect to the detector in order to acquire images of the breast at various different angles.

The possibility of performing tomosynthesis on the same system, in prone or vertical position, also makes it possible to use the tomosynthesis image to identify the target volume with greater accuracy than conventional stereotaxic biopsy.

The apparatus 1 can be configured to calculate, on the basis of the images acquired at different angles, the coordinates of the portion of volume in which a suspicious tissue is present and an optimized trajectory for the biopsy probe so that the needle of the probe reaches the abnormality and extracts the tissue by incision.

The invention described above is susceptible to industrial application and may be modified and adapted in several ways without thereby departing from the scope of the inventive concept. Moreover, all the details of the invention may be substituted for technically equivalent elements.

What is claimed is:

1. An apparatus for carrying out a biopsy on a breast of a patient, comprising:
   an analysis head including a radiation detector, the radiation detector configured to receive and detect on a detection plane radiation passing through the breast:
   a first frame including a floor support, the floor support including a pair of telescopic columns which support the first frame and define with the first frame substantially a portal structure;
   a separate second frame supporting the analysis head;
   a separate third frame connected to and supporting the second frame;
   a first rotational mount rotationally connecting the third frame to the first frame around an axis Y so that the third frame and analysis head is rotatable around the axis Y between 1) a substantially horizontal position, in which an operator can carry out the examination on the patient's breast while the patient is in a prone position, and 2) a substantially vertical position, in which an operator can carry out the examination on the patient's breast while the patient is in an upright position;
   a movement mechanism for rotating the third frame with respect to the first frame between the horizontal position and the vertical position, the movement mechanism including, a first power-driven actuator connected to the first frame and to the third frame to move the third frame with respect to the first frame;
   the second frame comprising a first portion supporting the radiation detector and a second portion supporting a radiation source,
   a second rotational mount rotationally connecting the first portion to the second portion to provide an axis of rotation R between the second portion and the first portion such that the radiation source is movable along an arcuate path at least partially surrounding the radiation detector to allow positioning of the radiation source in a plurality of positions with respect to the radiation detector;
   a second power-driven actuator connected between the first portion and the second portion for rotating the second portion supporting the radiation source with respect to the first portion supporting the radiation detector;
   a third rotational mount rotationally connecting the second frame to the third frame and providing the second frame with an axis K of rotation with respect to the third frame, the axis K of rotation being parallel to the axis of rotation R;
   a third power-driven actuator connected between the second frame and the third frame for rotationally moving the second frame with respect to the third frame around the axis K of rotation;
   the axis of rotation R being positioned between the radiation detector and the axis K of rotation;
   the axis Y being orthogonal with respect to the axis K of rotation;
   a biopsy probe movably attached to the second frame for performing the biopsy.

2. The apparatus according to claim 1, wherein the radiation detector is configured to detect X-rays.

3. The apparatus according to claim 2, wherein the radiation source is an X-ray source, which emits the X-rays towards the detection plane.

4. The apparatus according to claim 1, in which the second frame is rotatingly supported by the third frame to allow rotation of the second frame around the axis K of rotation perpendicular to the axis Y of rotation, the axis Y of rotation being horizontal.

5. The apparatus according to claim 4, comprising a motor for rotating the second frame with respect to the third frame.

6. The apparatus according to claim 1, wherein the axis Y is horizontal.

7. The apparatus according to claim 1, comprising at least one spring piston hinged to the first frame and to the third frame to exert a thrust on the third frame in order to move the third frame to the vertical position.

8. The apparatus according to claim 1, comprising an actuator configured to move the first frame vertically with respect to a ground.

9. The apparatus according to claim 1, wherein the first portion includes a U-shaped portion defining a channel receiving a portion of the second portion and the second power-driven actuator is a linear actuator including a piston sliding in a cylinder.

10. The apparatus according to claim 9, wherein either the piston or the cylinder is hinged to the first frame and the other between the piston and the cylinder is hinged to the third frame.

11. The apparatus according to claim 9, wherein the first power-driven actuator includes a first motor and the third power-driven actuator includes a second motor and a gear box connected between the second motor and the second frame.

12. The apparatus according to claim 11, wherein the first power-driven actuator includes a belt drive connecting the first motor between the first frame and the second frame.

13. A diagnostic system comprising an apparatus according to claim 1 and a bed with a patient support surface including an opening to allow the patient, in a face down position, to place the breast through the opening.

14. An apparatus for carrying out a biopsy on a breast of a patient, comprising:
   an analysis head including a radiation detector, the radiation detector configured to receive and detect on a detection plane radiation passing through the breast:
   a first frame including a floor support;
   a separate second frame supporting the analysis head;
   a separate third frame connected to and supporting the second frame;
   a first rotational mount rotationally connecting the third frame to the first frame around an axis Y so that the third frame and analysis head is rotatable around the axis Y between 1) a substantially horizontal position, in which an operator can carry out the examination on the patient's breast while the patient is in a prone position, and a substantially vertical position, in which an operator can carry out the examination on the patient's breast while the patient is in an upright position;
   a movement mechanism for rotating the third frame with respect to the first frame between the horizontal position and the vertical position, the movement mechanism including, a first power-driven actuator connected to the first frame and to the third frame to move the third frame with respect to the first frame;

the second frame comprising a first portion supporting the radiation detector and a second portion supporting a radiation source, a second rotational mount rotationally connecting the first portion to the second portion to provide an axis of rotation R between the second portion and the first portion such that the radiation source is movable along an arcuate path at least partially surrounding the radiation detector to allow positioning of the radiation source in a plurality of positions with respect to the radiation detector;

a second power-driven actuator connected between the first portion and the second portion for rotating the second portion supporting the radiation source with respect to the first portion supporting the radiation detector;

a third rotational mount rotationally connecting the second frame to the third frame and providing the second frame with an axis K of rotation with respect to the third frame, the axis K of rotation being parallel to the axis of rotation R;

a third power-driven actuator connected between the second frame and the third frame for rotationally moving the second frame with respect to the third frame around the axis K of rotation;

the axis of rotation R being positioned between the radiation detector and the axis K of rotation;

the axis Y being orthogonal with respect to the axis K of rotation;

a biopsy probe movably attached to the second frame for performing the biopsy.

15. The apparatus according to claim 14, wherein the first portion includes a U-shaped portion defining a channel receiving a portion of the second portion and the second power-driven actuator is a linear actuator including a piston sliding in a cylinder.

16. The apparatus according to claim 15, wherein the first power-driven actuator includes a first motor and the third power-driven actuator includes a second motor and a gear box connected between the second motor and the second frame.

17. The apparatus according to claim 16, wherein the first power-driven actuator includes a belt drive connecting the first motor between the first frame and the second frame.

* * * * *